United States Patent [19]

Strnadova et al.

[11] 4,447,540

[45] May 8, 1984

[54] MICROORGANISM STRAIN OF SPECIES CLAVICEPS PURPUREA

[75] Inventors: Karin Strnadova; Jan Kybal; Eduard Svoboda, all of Prague; Jiri Spacil, Opava, all of Czechoslovakia

[73] Assignee: SPOFA, spojene podniky prozdravotnickou vyrobu, Prague, Czechoslovakia

[21] Appl. No.: 400,037

[22] Filed: Jul. 20, 1982

[30] Foreign Application Priority Data

Jul. 28, 1981 [CS] Czechoslovakia .................. 5731-81

[51] Int. Cl.³ ...................... C12N 1/14; C12P 17/18; C12R 1/645

[52] U.S. Cl. .................................. 435/254; 435/119; 435/911

[58] Field of Search ................. 435/119, 254

[56] References Cited

U.S. PATENT DOCUMENTS 3,884,762 5/1975 Wack et al. ......................... 435/119
4,369,252 1/1983 Wack et al. ......................... 435/119

Primary Examiner—Alvin E. Tanenholtz

[57] ABSTRACT

A new microorganism strain of species *Claviceps purpurea* (Fr.) Tul. CCM F-725 producing ergocornine and ergocryptine.

1 Claim, No Drawings

MICROORGANISM STRAIN OF SPECIES CLAVICEPS PURPUREA

This invention relates to a new microorganism strain of species *Claviceps purpurea,* identified as (Fr.) Tul. CCM F-725. This strain was produced by long-term improving of the production strain employed for the field production of ergot containing ergocornine and ergocryptine up to the year 1974 (K. Strnadova, J. Kybal, Folia Microbiol. 19, 272, 1974). In the course of this improving, strain CCM F-508 (Czechoslovak Author's Certificate No. 176,803) was obtained; this strain is used for field production as well. This strain also belongs to the ergocornine-ergocryptine chemical race, and it produces in field culture sclerotia containing 0.5% by weight of alkaloids in dry matter on the average, the mutual weight ratio of both named alkaloids (ergocornine and ergocryptine) being 6:4 to 4:6, respectively.

The drawbacks of the up-to-now-used strain CCM F-508 are its relatively low content of alkaloids and above all also the unfavorable ratio between the content of both ergocryptine components, that is α-ergocryptine and β-ergocryptine, strongly shifted toward α-ergocryptine. Ergocryptine is an important medical substance and starting compound for the preparation of derivatives and the medical forms produced from them. Medical forms having an exactly defined weight ratio of α- and β-ergocryptine have been recently enforced in therapy, that is, the ratio 1.5:1 to 2.5:1, which forms ensure standard therapeutic effects. Due to the unfavorable weight ratio of both these components in ergot sclerotia of the production strain CCM F-508 (9:1), ergot of this type became a disadvantageous raw material for making the desired preparations.

In the course of improving the original strain, an auxotrophic asporogenous mutant was selected after the mutagenic treatment with nitrous acid of the strain CCM F-508; this mutant is able to synthesize alkaloids not only in a parasitic but also in a saprophytic culture. In the further course of improving this mutant, a spontaneously originated suppressor mutant was isolated which kept the mentioned production signs and with which renewal of the ability of conidia formation took place simultaneously with a return to prototrophy.

The new strain, which is an object of the present invention, was obtained by further improving the above-mentioned mutant using usual mutagenic treatments as follows:

(1) Conidia were subjected to the effect of nitrous acid having the concentration of 0.0030 to 0.0045 M (depending on conidia sensitivity) under mixing for 5 minutes. The conidia were then centrifuged, washed with water, and sown on a current medium and tested for production of alkaloids. The effect of nitrous acid was repeated 6 times altogether.

(2) There was further employed the action of ethylmethane sulphonate in a concentration of 0.01 M in a conidia suspension under stirring for 5 hours. After this time the conidia were washed, sown on a current medium, and tested for the production of alkaloids. This treatment was repeated 3 times.

(3) As the third mutagen, 5-bromouracil was added in a concentration of 0.4% by weight together with 0.1% by weight of sulphathiazole into a completely inoculated medium. Cultivation took place for 14 days at a temperature of 24 degrees C.

Conidia were collected from grown cultures and isolates from them were further tested for the production of alkaloids. As far as it was suitable, selections of mono-conidial cultures without mutation were inserted.

The new strain was deposited in the Czechoslovak Collection of Microorganisms of the J. E. Purkyne University, Brno, Obrancu miru 10, under the number CCM F-725.

The strain *Claviceps purpurea* (Fr.) Tul. CCM F-725 is prototrophic. It is able thus to grow under parasitic conditions upon a rye spike, and also under saprophytic conditions in a stationary culture in a liquid medium. In both cases it produces alkaloids.

On a hardened complete medium (brewer's wort 5 degrees Be, acidic hydrolyzate of casein 1% by weight, crystalline magnesium sulphate 0.1% by weight, agar 3% by weight, pH 6.3) inoculated by spreading a conidia suspension, the surface of the medium is frown full at a temperture of 25 degrees C. within 4 to 5 days, and then an air mycelium is formed, throttling numerous conidia. Hyphae are typically sphacelous, long, little branched and rarely partitioned. The cells are thin-walled and they have a low content of fatty inclusions. Mycelium is purple pigmented at the bottom side in later evolution phases; air mycelium is without pigment. Conidiation is complete after 21 days of incubation. The conidia are oval, as a rule 4 to 7 μm long and 3 to 5 μm wide, thin-walled and mononuclear. After being sown on fresh medium of the same composition, they germinate within 24 to 48 hours, most frequently on one, rarely on both poles. One culture in a test tube of the size 20×200 mm contains approximately $3.0\times10^9$ of conidia.

At the level of liquid production medium (saccharose 25% by weight, corn-steep-liquor 0.44% by weight, potassium dihydrogen phosphate 0.06% by weight, citric acid 0.946% by weight, crystalline calcium nitrate 0.16% by weight, crystalling magnesium sulphate 0.11% by weight, pH 6.8 adjusted using ammonia) the strain grows in the course of 21 days of lasting incubation at a temperature of 24 degrees C. in compact bent sclerotial mycelium pigmenting yellow-brown to brown-purple, which mycelium grows on at the lower side and throttles conidia at the upper side. The hyphae are short and wide, cells are nearly isodiametric, thick-walled with high content of fat. Conidia have properties similar to those with a hardened complete medium only their dimensions have usually smaller variations.

Elongated sclerotia are formed in a parasitic culture upon a rye spike, as a rule 2 to 6 mm thick and 10 to 30 mm long, straight or sickle-shaped being narrowed in the direction of the apical end. The coloring of matured sclerotia is brown-red at the surface and white with a yellow tinge on fracture.

According to the spectrum of the produced alkaloids, the new strain belongs to the chemical rage ergocornine-ergocryptine. Ergocornine and ergocryptine in the weight ratio of approximately 1:1 are the main alkaloids contained in both the parasitic ergot sclerotia and the mycelium of saprophytic culture. The ergocryptine component is formed by α-ergocryptine and β-ergocryptine in parasitic sclerotia in a weight ratio of approximately 2:1 to 1:1, and in saprophytic mycelium without precursoring in a weight ratio of approximately 5:1. Customary ergometrine and futher a small amount of ergosine and traces of ergocristine, ergotamine, lysergylvaline amide, ergoxine (ergostine, ergonine, ergoptine) and of further three nonidentified alkaloids are the components of the alkaloid spectrum besides the above set forth main alkaloids.

A high production of alkaloids is a significant sign of the new strain according to the invention, and that is so with both parasitic and saprophytic cultivation. Sclerotia from parasitic culture as well as saprophytically grown mycelium contains up to 1.5% by weight of total alkaloids. A further fraction of alkaloids is additionally released into the production medium in the course of surface saprophytic cultivation, which medium contains up to 250 g/ml of alkaloids (expressed as ergometrine) after the fermentation is completed.

Although the invention is described with reference to one preferred embodiment thereof, it is to be expressly understood that it is in no way limited to the disclosure of such preferred embodiment but is capable of numerous modifications within the scope of the appended claims.

We claim:

1. Biologically pure culture of *Claviceps purpurea* (Fr.) Tul. variant strain CCM F-725 which can be fermented to produce ergocornine, alpha-ergocryptine